(12) United States Patent
Schulz

(10) Patent No.: US 6,391,104 B1
(45) Date of Patent: May 21, 2002

(54) PERYLENE PIGMENT COMPOSITIONS

(75) Inventor: Gregory R. Schulz, Mt. Pleasant, SC (US)

(73) Assignee: Bayer Corporation, Pittsburgh, PA (US)

( * ) Notice: Subject to any disclaimer, the term of this patent is extended or adjusted under 35 U.S.C. 154(b) by 0 days.

(21) Appl. No.: 09/729,257

(22) Filed: Dec. 1, 2000

(51) Int. Cl.[7] ................... C07D 221/18; C07D 401/00; C09B 67/22
(52) U.S. Cl. ........................................ 106/494; 106/498
(58) Field of Search ................................ 106/493, 494, 106/498; 546/37

(56) References Cited

U.S. PATENT DOCUMENTS

| | | | |
|---|---|---|---|
| 2,473,015 A | 6/1949 | Cullinan et al. | 260/282 |
| 4,336,383 A | 6/1982 | Vorozhtsov et al. | 546/52 |
| 4,556,662 A | 12/1985 | Neumann et al. | 430/58 |
| 4,714,666 A | 12/1987 | Wiedemann et al. | 430/59 |
| 4,762,569 A | 8/1988 | Miki et al. | 106/476 |
| 4,968,571 A | 11/1990 | Gruenbaum et al. | 430/58 |
| 5,019,473 A | 5/1991 | Nguyen et al. | 430/58 |
| 5,104,918 A | 4/1992 | Bäbler | 524/90 |
| 5,248,774 A | 9/1993 | Dietz et al. | 544/125 |
| 5,508,137 A | 4/1996 | Langhals | 430/78 |
| 5,650,513 A | 7/1997 | Langhals et al. | 546/38 |
| 5,958,129 A | 9/1999 | Urban et al. | 106/498 |
| 6,015,458 A | 1/2000 | Schulz et al. | 106/498 |
| 6,022,656 A | 2/2000 | Visser et al. | 430/58.65 |
| 6,039,769 A | 3/2000 | Schulz et al. | 8/574 |

FOREIGN PATENT DOCUMENTS

| | | |
|---|---|---|
| DE | 299 733 | 5/1992 |
| WO | 00/40657 | 7/2000 |

OTHER PUBLICATIONS

W. Herbst & K. Hunger, Industrial Organic Pigments, 2$^{nd}$ ed (New York: VCH Publishers Inc. month unavailable, 1997), pp. 9 and 476–479 Perylene and Perinone Pigments.

H. Zollinger, Color Chemistry (VCH Verlagsgessellschaft, month unavailable, 1991) pp. 227–228 and 296–298, Syntheses, Properties and Applications of Organic Dyes and Pigments.

M.A. Perkins, "Pyridines and Pyridones" in The Chemistry of Synthetic Dyes and Pigments, ed. H.A. Lubs(Malabar, Florida: Robert E. Krieger Publishing Company, month unavailable, 1955), pp. 481–482.

K. Merkle and H. Schäfer, "Surface Treatment of Organic Pigments" in Pigment Handbook, vol. III (New York: John Wiley & Sons, Inc. month unavailable 1973), pp. 157–167.

R.B. McKay, "The Development of Organic Pigments with Particular Reference to Physical Form and Consequent Behaviour in Use" in Rev. Prog. Coloration, 10, pp. 25–32, (month unavailable) 1979.

R.B. McKay, "Control of the application performance of classical organic pigments", in JOCCA, (month unavailable) 1989, pp. 89–93.

T. Deligerorgiev et al, "Synthesis and Properties of Fluorescent Bis–Quaternized Perylene Dyes" in Dyes and Pigments, 24, pp. 75–81 (month unavailable) 1994.

H. Langhals et al, "Imidazoleperylenimide–ein stark fluoreszierender, stabiler Ersatz für Terrylen" in Angew. Chem., 111, pp. 143–144 (month unavailable) 1999.

(List continued on next page.)

*Primary Examiner*—Anthony Green
(74) *Attorney, Agent, or Firm*—Joseph C. Gil; Richard E. L. Henderson; Thomas W. Roy

(57) ABSTRACT

This invention relates to perylene pigment compositions containing a reactive co-precipitated blend of (1) about 75 to about 99.9 mol %, relative to the pigment composition, of a compound having the formula (I)

(I)

wherein

R is hydrogen, $C_1$–$C_6$ alkyl, $C_5$–$C_8$ cycloalkyl, $C_7$–$C_6$ aralkyl, or $C_6$–$C_{10}$ aryl, A is $C_1$–$C_6$ alkyl, $C_1$–$C_6$ alkoxy, a sulfonyl group, amino, ammonium, hydroxy, nitro, or halogen, and m is zero or a number from 1 to 8; and (2) about 0.1 to about 25 mol %, relative to the pigment composition, of a perylene dicarboxamidine imide having the formula (II)

(II)

wherein

W is optionally substituted or modified $C_2$–$C_3$ alkylene, and

R, A, and m are defined as above.

10 Claims, No Drawings

OTHER PUBLICATIONS

Heinz Langhals, "Novel Dyes for Electrophotographic Process with Perylene Structure Element" in IS&T's Tenth International Congress on Advance in Non–Impact Printing Technologies, pp. 192–195, (month unavailable) 1994.

Y. Nagao, "Synthesis and properties of perylene pigments" in Progress in Organic Coatings, 31, pp. 43–49, (month unavailable), 1997.

H. Quante et al, "Synthesis of Soluble Perylenebisamidine Derivatives. Novel Long–Wavelength Absorbing and Fluorescent Dyes" in Chem. Mater., 9, pp. 495–500, (month inavailable) 1997.

H. Langhals, "Novel Perylene Derivatives as Highly Photostable Fluorescent Dyes" in Chimia, 48, pp. 503–504 (month unavailable) 1994.

G. Tamizhmani et al, "Photoelectrochemical Characterization of Thin Films of Perylenetracarboxylic Acid Derivatives" in Chem. Mater., 3, pp. 1046–1053, (month unavailable) 1991.

Y. Nagao et al, "Synthesis of Unsymmetrical Perylenebis-(discarboximide) Derivatives" in Chemistry Letters, pp. 151–154, (month unavailable) 1979.

K. Venkataraman et al, "Anthraquinonoid Vat Dyes" in Chemistry of Synthetic Dyes ed. 5, (New York Academic Press, month unavailable, 1971), ed. K. Venkataraman, p. 233.

L. Feiler et a, "Synthesis of Perylene–3,4–dicarboximides— Novel Highly Photostable Fluroescent Dyes" in Liebigs Ann., pp. 1229–1244, (month unavailable) 1995.

PERYLENE PIGMENT COMPOSITIONS

BACKGROUND OF THE INVENTION

This invention relates to perylene pigment compositions containing, in addition to a perylene pigment component, certain asymmetric perylene dicarboxamidine imides that serve as crystal growth inhibitors during the preparation of the pigment compositions.

Perylenes, including diimides of perylene-3,4,9,10-tetracarboxylic acid, can be prepared by methods known in the art. E.g., W. Herbst and K. Hunger, *Industrial Organic Pigments,* 2nd ed. (New York: VCH Publishers, Inc., 1997), pages 9 and 476–479; H. Zollinger, *Color Chemistry* (VCH Verlagsgessellschaft, 1991), pages 227–228 and 297–298; and M. A. Perkins, "Pyridines and Pyridones" in *The Chemistry of Synthetic Dyes and Pigments,* ed. H. A. Lubs (Malabar, Fla.: Robert E. Krieger Publishing Company, 1955), pages 481–482. However, perylenes as initially isolated, often referred to as crude perylenes, are generally unsuitable for use as pigments and thus must be subjected to one or more additional finishing steps that modify particle size, particle shape, and/or crystal structure in such a way that provides good pigmentary quality. See, for example, K. Merkle and H. Schäfer, "Surface Treatment of Organic Pigments" in *Pigment Handbook,* Vol. III (New York: John Wiley & Sons, Inc., 1973), page 157; R. B. McKay, "The Development of Organic Pigments with Particular Reference to Physical Form and Consequent Behavior in Use" in *Rev. Prog. Coloration,* 10, 25–32 (1979); and R. B. McKay, "Control of the application performance of classical organic pigments" in *JOCCA,* 89–93 (1989).

Perylene diimides in which at least one of the imide groups is derived from a diamine that does not further react to form a dicarboxamidine imide are known. E.g., U.S. Pat. Nos. 5,958,129 and 5,248,774; European Patent Application EP 283,436; and T. Deligeorgiev et al, "Synthesis and Properties of Fluorescent Bis-Quaternized Perylene Dyes" in *Dyes and Pigments,* 24, 75–81 (1994).

Symmetric perylenes in which both of the imide groups are in the form of a dicarboxamidine have been reported. E.g., U.S. Pat. Nos. 4,556,622 and 2,473,015. These patents do not describe asymmetric perylene diimides in which only one of the imide groups is in the form of a dicarboxamidine.

Asymmetric perylene diimides in which one of the imide groups is in the form of a dicarboxamidine group have been reported but are not described as being used in admixture with perylene pigments. E.g., U.S. Pat. Nos. 5,508,137 and 4,714,666; German Patentschrift DD 299,733; H. Langhals et al, "Imidazoleperylenimide—ein starck fluoreszierender, stabiler Ersatz für Terrylen" in *Angew. Chem.,* 111, 143–144 (1999); "Novel Dyes for Electrophotographic Processes with Perylene Structure Element" in *IS&T's Tenth International Congress on Advances in Non-impact Printing Technologies,* 192–195 (1994); Y. Nagao, "Synthesis and properties of perylene pigments" in *Progress in Organic Coatings,* 31, 43–49 (1997); H. Quante et al, "Synthesis of Soluble Perylenebisamidine Derivatives. Novel Long-Wavelength Absorbing and Fluorescent Dyes" in *Chem. Mater.,* 9, 495–500 (1997); H. Langhals, "Novel Perylene Derivatives as Highly Photostable Fluorescent Dyes" in *Chimia,* 48, 503–505 (1994); G. Tamizhmani et al, "Photoelectrochemical Characterization of Thin Films of Perylenetetracarboxylic Acid Derivatives" in *Chem. Mater.,* 3, 1046–1053 (1991); Y. Nagao et al, "Synthesis of Unsymmetrical Perylenebis(dicarboximide) Derivatives" in *Chemistry Letters,* 151–154 (1979); K. Venkataraman et al, "Anthraquinonoid Vat Dyes" in *Chemistry of Synthetic Dyes,* ed. K. Venkataraman, 5 (New York: Academic Press, 1971), page 233. Some of the compounds have been prepared by unrelated synthetic methods. E.g., U.S. Pat. No. 4,336,383.

Perylene dicarboxamidines derived from perylene dicarboxylic compounds rather than perylene tetracarboxylic compounds are also known but have not been described as being used in admixture with perylene pigments. E.g., U.S. Pat. No. 5,650,513 and L. Feiler et al, "Synthesis of Perylene-3,4-dicarboximides—Novel Highly Photostable Fluorescent Dyes" in *Liebigs Ann.,* 1229–1244 (1995).

Perylene dicarboxamidine hydrazamides are known and have been described as being used in admixture with perylene pigments. See PCT application WO 00/40657. However, the hydrazamide moiety is structurally different from the imide moiety of the perylene dicarboxamidine imides of the present invention, and the PCT application does not disclose the preparation of co-precipitated blends of perylene diimides and perylene dicarboxamidine hydrazamides.

Compositions containing mixtures of perylene diimides and perylene dicarboxamidine imides are known. For example, U.S. Pat. Nos. 6,022,656, 5,019,473, and 4,968,571 describe blending the separately prepared components in polymeric binders for use in electrophotographic elements and U.S. Pat. No. 4,762,569 describes dispersing the separately prepared components non-aqueous paints or inks. None of these patents describes the preparation of co-precipitated blends of perylene diimides and perylene dicarboxamidine imides having small particle sizes of uniform particle size distribution.

It has now surprisingly been found that reactive co-precipitation of perylene pigments with certain asymmetric perylene dicarboxamidine imides provides pigment compositions having small-sized crystals that exhibit improved transparency and color properties, even in the unfinished form that is initially isolated without further physical manipulation to modify crystal size.

SUMMARY OF THE INVENTION

This invention relates to perylene pigment compositions comprising a reactive co-precipitated blend comprising (1) about 75 to about 99.9 mol % (preferably about 90 to about 99.5 mol %), relative to the pigment composition, of a compound having the formula (I)

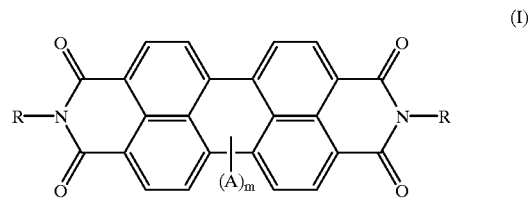

wherein
each R is independently hydrogen, $C_1$–$C_6$ alkyl, $C_5$–$C_8$ cycloalkyl, $C_7$–$C_{16}$ aralkyl, or $C_6$–$C_{10}$ aryl (preferably where both R groups are the same),
A is $C_1$–$C_6$ alkyl, $C_1$–$C_6$ alkoxy, a sulfonyl group, amino, ammonium, hydroxy, nitro, or halogen, and
m is zero or a number from 1 to 8; and (2) about 0.1 to about 25 mol % (preferably about 0.5 to about 10 mol %), relative to the pigment composition, of an asymmetric perylene dicarboxamidine imide having the formula (II)

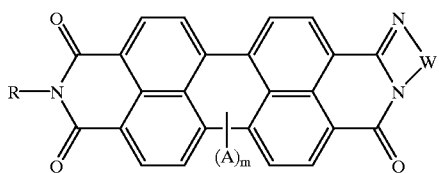

(II)

wherein
W is $C_2$–$C_3$ alkylene that is optionally substituted or modified,
R is hydrogen, $C_1$–$C_6$ alkyl, $C_5$–$C_8$ cycloalkyl, $C_7$–$C_{16}$ aralkyl, or $C_6$–$C_{10}$ aryl,
A is $C_1$–$C_6$ alkyl, $C_1$–$C_6$ alkoxy, a sulfonyl group, amino, ammonium, hydroxy, nitro, or halogen, and
m is zero or a number from 1 to 8.

This invention further relates to a process for the preparation of such perylene pigment compositions comprising
(a) reacting
(i) a perylene tetracarboxylic compound having the formula (III)

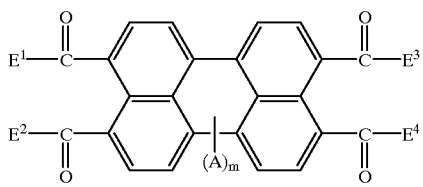

(III)

wherein
$E^1$ and $E^2$ are independently $OR^1$ or together are O or NR,
$E^3$ and $E^4$ are independently $OR^1$ or together are O,
each $R^1$ is independently $C_1$–$C_6$ alkyl (i.e., for alkyl esters), $C_7$–$C_{16}$ aralkyl (i.e., for aralkyl esters), or $C_6$–$C_{10}$ aryl (i.e., for aryl esters),
R is hydrogen, $C_1$–$C_6$ alkyl, $C_5$–$C_8$ cycloalkyl, $C_7$–$C_{16}$ aralkyl, or $C_6$–$C_{10}$ aryl,
A is $C_1$–$C_6$ alkyl, $C_1$–$C_6$ alkoxy, a sulfonyl group, amino, ammonium, hydroxy, nitro, or halogen, and
m is zero or an integer of from 1 to 8,
(ii) about 0.1 to about 25 mol % (preferably 0.5 to 10 mol %), based on the total amount of component (a)(i), of a diamine having the formula (IV)

$H_2N$—W—$NH_2$ (IV)

wherein W is $C_2$–$C_3$ alkylene that is optionally substituted or modified, and
(iii) optionally, a solvent, thereby forming an intermediate composition;
(b) reacting
(i) the intermediate composition from step (a),
(ii) a molar excess, relative to the intermediate composition (preferably about 2.1 to about 5 mol per mol of the intermediate composition), of an amine having the formula (V)

R—$NH_2$ (V)

wherein R is hydrogen (i.e., ammonia), $C_1$–$C_6$ alkyl, $C_5$–$C_8$ cycloalkyl, $C_7$–$C_{16}$ aralkyl, or $C_6$–$C_{10}$ aryl (optionally where R in formula (V) is different from R in formula (III)), and
(iii) optionally, a solvent,
thereby forming the perylene pigment composition as a reactive co-precipitated blend comprising a compound of formula (I) and an asymmetric perylene dicarboxamidine imide of formula (II); and
(c) isolating the perylene pigment composition.

DETAILED DESCRIPTION OF THE INVENTION

Perylene tetracarboxylic compounds that can be used according to this invention, some of which are crude or conditioned perylene pigments and some of which are precursors of perylene pigment, can be prepared by any of various methods known in the art. E.g., W. Herbst and K. Hunger, *Industrial Organic Pigments,* 2nd ed. (New York: VCH Publishers, Inc., 1997), pages 9 and 476–479; H. Zollinger, *Color Chemistry* (VCH Verlagsgessellschaft, 1991), pages 227–228; M. A. Perkins, "Pyridines and Pyridones" in *The Chemistry of Synthetic Dyes and Pigments,* ed. H. A. Lubs (Malabar, Fla.: Robert E. Krieger Publishing Company, 1955), pages 481–482; and F. Graser, "Perylenes" in *Pigment Handbook,* 2nd edition, Vol. III (New York: John Wiley & Sons, Inc., 1988), pages 653–658.

As used herein, the term "$C_2$–$C_3$ alkylene" refers to optionally substituted or modified 1,2-ethylene or 1,3-propylene groups that, when referring to the perylene dicarboxamidine imides of formula (II), are attached to two nitrogen atoms to form the indicated heterocyclic ring and, when referring to the diamine reactants of formula (IV), are attached to two $NH_2$ groups.

Substituted $C_2$–$C_3$ alkylene groups are those in which one or more of the ethylene or propylene carbon atoms are each substituted with one or two $C_1$–$C_6$ alkyl (preferably methyl), $C_1$–$C_6$ alkoxy, $C_5$–$C_8$ cycloalkyl, $C_7$–$C_{16}$ aralkyl, $C_6$–$C_{10}$ aryl (preferably phenyl), or halogen group or with one sulfonyl, amino, ammonium, hydroxy, or nitro group; in which one or more of the ethylene or propylene carbon atoms is gem-disubstituted with a $C_3$–$C_7$ alkylene group to form a geminal ring system having 4 to 8 ring carbon atoms; or in which adjacent carbon atoms are part of a fused-on ring system. The term "fused-on ring systems" refers to ethylene or propylene groups in which two adjacent carbon atoms are substituted with groups that together form a fused-on hydrocarbon ring, including a cycloalkane ring or, more preferably, an aromatic ring system such as benzene or 1,2- or 2,3-naphthalene or refers to a propylene group in which all three carbon atoms are substituted with groups that together form a fused-on multiple hydrocarbon ring (most preferably a polyaromatic ring system such as 1,8-naphthalene). Each of the geminal or fused-on ring systems can be ring-substituted, for example, with $C_1$–$C_6$ alkyl, $C_7$–$C_{16}$ aralkyl, $C_6$–$C_{10}$ aryl, $C_1$–$C_6$ alkoxy, sulfonyl, amino, ammonium, and halogen groups such as described above.

Modified $C_2$–$C_3$ alkylene groups are those in which one or more of the carbon atoms is replaced with O, S, or $NR^a$ (wherein $R^a$ is hydrogen or $C_1$–$C_6$ alkyl). An example of a diamine based on a modified alkylene group of this type is diaminoguanidine.

Preferred $C_2$–$C_3$ alkylene groups include unsubstituted and unmodified 1,3-propylene or 1,3-propylene in which one or more carbon atoms are each substituted with one or two $C_1$–$C_6$ alkyl groups.

The term "$C_1$–$C_6$ alkyl" refers to aliphatic hydrocarbon groups having from 1 to 6 carbon atoms. Examples of $C_1$–$C_6$ alkyl are methyl, ethyl, propyl, butyl, pentyl, hexyl, and the isomeric forms thereof. The term "$C_5$–$C_8$ cycloalkyl" refers to cycloaliphatic hydrocarbon groups having from 5 to 8 carbon atoms. Examples of $C_5$–$C_8$ cycloalkyl are cyclopentyl, cyclohexyl, cycloheptyl, and cyclooctyl. The term "$C_6$–$C_{10}$ aryl" refers to phenyl and 1- or 2-naphthyl. The term "$C_7$–$C_{16}$ aralkyl" refers to $C_1$–$C_6$ alkyl substituted with $C_6$–$C_{10}$ aryl such that the total number of carbon atoms is from 7 to 16. Examples of $C_7$–$C_{16}$ aralkyl are benzyl, phenethyl, and naphthylmethyl. These alkyl, cycloalkyl, aryl, and aralkyl groups can be substituted at one or more carbon atoms with $C_1$–$C_6$ alkyl (which, if the primary group is alkyl, can create a branched or long-chain alkyl group), $C_1$–$C_6$ alkoxy, $C_7$–$C_{16}$ aralkyl, $C_7$–$C_{16}$ aralkoxy, $C_6$–$C_{10}$ aryl, $C_6$–$C_{10}$ aryloxy, amino (such as amino substituted with one or more $C_1$–$C_6$ alkyl, $C_7$–$C_{16}$ aralkyl, and/or $C_6$–$C_{10}$ aryl groups), halogen, hydroxy (including tautomeric oxo forms), alkoxycarbonyl, aryloxycarbonyl, cyano, and nitro groups. Aromatic rings of aryl and aralkyl groups can also be substituted with groups, such as aryl-N=N-groups, that are typically not stable when attached to aliphatic carbon atoms. The term "$C_1$–$C_6$ alkoxy" refers to straight or branched chain alkyl oxy groups having from 1 to 6 carbon atoms. Examples of $C_1$–$C_6$ alkoxy are methoxy, ethoxy, propoxy, butoxy, pentyloxy, hexyloxy, and the isomeric forms thereof. The term "$C_7$–$C_{16}$ aralkoxy" refers to $C_1$–$C_6$ alkoxy substituted with $C_6$–$C_{10}$ aryl such that the total number of carbon atoms is from 7 to 16. An example of $C_7$–$C_{16}$ aralkoxy is benzyloxy. The term "$C_6$–$C_{10}$ aryloxy" refers to phenoxy and 1- or 2-naphthoxy, in which the aromatic portion can optionally be substituted as described above for aryl groups. The term "sulfonyl group" refers to —$SO_2$—$R^i$ groups, such as alkylsulfonyl (in which $R^i$ is alkyl; for example, methanesulfonyl or ethanesulfonyl), arylsulfonyl (in which $R^i$ is aryl; for example, benzenesulfonyl, 1- or 2-naphthalenesulfonyl, and substituted forms such as toluenesulfonyl), sulfoxyl and corresponding esters (in which $R^i$ is OH, alkoxy, cycloalkoxy, aralkoxy, aryloxy), and sulfonamides (in which $R^i$ is —$NR^{ii}R^{iii}$, wherein $R^{ii}$ and $R^{iii}$ are independently hydrogen, alkyl, cycloalkyl, aralkyl, or aryl). The terms "amino" and "ammonium" refer respectively to —$NR^{iv}R^v$ and —$NR^{iv}R^vR^{vi+}$ in which $R^{iv}$, $R^v$, and $R^{vi}$ are independently hydrogen, $C_1$–$C_6$ alkyl, or $C_7$–$C_{16}$ aralkyl and each ammonium group is electrically balanced with a stoichiometric amount of an anion. The term "halogen" includes fluorine, chlorine, bromine, and iodine.

Perylene tetracarboxylic compounds that can be used as starting materials (a)(i) for the preparation of pigmentary perylene compositions of the invention include various carboxylic esters or cyclic anhydrides of formula (III). Preferred perylene tetracarboxylic compounds are dianhydrides of formula (III) in which $E^1$ and $E^2$ together and $E^3$ and $E^4$ together are oxygen atoms, which corresponds to compounds having the formula (IIIa)

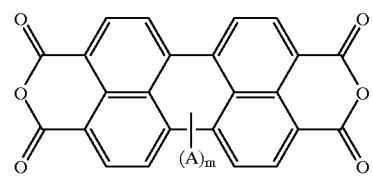

(IIIa)

wherein A and m are defined as above for formula (III). Particularly preferred perylene dianhydrides have no aromatic ring substituents A (i.e., m is zero), but substituted perylene dianhydrides in which at least one of the eight substitutable aromatic ring carbon atoms of the perylene moiety has at least one group A (i.e., where m is not zero) are also suitable. Suitable but generally less preferred perylene tetracarboxylic compounds include esters in which groups $E^1$, $E^2$, $E^3$, and $E^4$ are independently $C_1$–$C_6$ alkoxy, $C_7$–$C_{16}$ aralkoxy, or $C_6$–$C_{10}$ aryloxy (preferably tetracarboxylic esters in which $E^1$, $E^2$, $E^3$, and $E^4$ are identically alkoxy), particularly those having no aromatic ring substituents A (i.e., m is zero). It is, of course, also possible to use ester anhydrides in which, for example, $E^1$ and $E^2$ together are an oxygen atom and $E^3$ and $E^4$ are independently $C_1$–$C_6$ alkoxy.

Other suitable but generally less preferred perylene tetracarboxylic compounds are imide diesters or anhydrides of formula (III) in which $E^1$ and $E^2$ together are NR and $E^3$ and $E^4$ together are either $OR^1$ or (somewhat more preferably) an oxygen atom, which corresponds to compounds having the formula (IIIb)

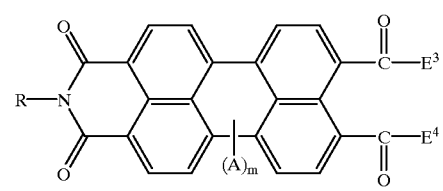

(IIIb)

wherein R, $R^1$, A, and m are defined as above for formula (III).

Some of the perylene tetracarboxylic compounds used as component (a)(i) can themselves be pigments but it is not necessary for these compounds to be pigments as long as the ultimate perylene pigment composition is pigmentary.

In step (a), a perylene tetracarboxylic compound of formula (III) is allowed to react with a diamine having the formula (IV) in amounts such that about 0.1 to about 25 mol % (preferably 0.5 to 10 mol %) of an asymmetric perylene dicarboxamidine imide of formula (II) is present in the ultimate pigment composition of the invention. In practice, this can be achieved by using 0.1 to about 25 mol % of the diamine relative to the total amount of the perylene tetracarboxylic compound and the diamine used in step (a).

Suitable diamines are compounds of formula (IV)

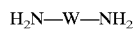 (IV)

in which W represents an optionally substituted or modified 1,2-ethylene or 1,3-propylene group. The ultimately formed asymmetric perylene dicarboxamidine imide of formula (II) will have a five-membered heterocyclic group if 1,2- diaminoethane or a derivative thereof is used in step (a) or a six-membered heterocyclic group if 1,3-diaminopropane or a derivative thereof is used. Particularly preferred diamines are unsubstituted and unmodified 1,3-diaminopropane or 1,3-diaminopropane substituted in the 2-position with one or two $C_1$–$C_6$ alkyl (preferably methyl) groups or a hydroxy group. Examples of suitable diaminopropanes include 1,3-diaminopropane, 2-methyl-1,3-diaminopropane, 2,2-dimethyl-1,3-diaminopropane, 1,3-diamino-2-hydroxypropane, and the like. Examples of suitable diaminoethanes include 1,2-diaminoethane, 1,2-diaminopropane, 1,2-diaminobutane, and the like. Although generally not preferred, it is possible to choose diamines in which substituents on group W can be converted to other substituents during or after step (b) or any subsequent step is carried out.

Step (a) is typically, although not necessarily, carried out in a solvent. Suitable solvents (a)(iii) are liquids that are capable of dissolving or suspending the components of the reaction mixture without significantly decomposing or otherwise reacting during the reaction. Examples of suitable solvents include water; monofunctional alcohols, particularly lower alkanols such as methanol, ethanol, butanol, pentanol, hexanol, and isomeric forms thereof; amides such as dimethylformamide and dimethylacetamide; ethers such as tetrahydrofuran and dioxane; alkylene glycols and thioglycols such as ethylene glycol, propylene glycol, butylene glycol, triethylene glycol, hexylene glycol, diethylene glycol, and thiodiglycol; polyalkylene glycols, such as polyethylene glycol and polypropylene glycol; other polyols, such as glycerol and 1,2,6-hexanetriol; lower alkyl ethers of polyhydric alcohols, such as 2-methoxyethanol, 2-(2-methoxyethoxy)ethanol, 2-[2-(2-methoxyethoxy)ethoxy]ethanol, and 2-[2-(2-ethoxyethoxy)ethoxy]ethanol; aromatic and heteroaromatic liquids, such as benzene, pyridine, and quinoline; and other such organic liquids known in the art. Water is a particularly preferred solvent. Other solvents can, of course, also often be used, but it is generally advisable to avoid solvents that can react with the reactive components. The quantity of solvent is generally not critical but should be an amount sufficient to dissolve or suspend the components of the reaction mixture but not so large as to require removal of excessive amounts after the reaction is complete. Typical quantities of solvent range from about 0.5 to about 100 parts by weight (preferably 1 to 10 parts by weight) relative to the total amount of components (a) and (b).

Solvents (a)(iii) may not be necessary if either of components (a)(i) or (a)(ii) is a liquid or if the mixture of components can be melted without significant decomposition to undesired by-products.

Conventional additives used with perylene pigments can also be added before or during reaction step (a). Suitable additives include, for example, surfactants, dispersants, wetting agents, defoamers, grinding aids, latices, organic pigment derivatives, inorganic compounds (such as metal salts), or mixtures thereof. Examples of such optional ingredients include sulfonic acid, sulfonamide, carboxamide, aminoalkyl, or phthalimidoalkyl derivatives of organic pigments (particularly of perylenes, phthalocyanines, or quinacridones); acrylic copolymers; fatty acids having at least 12 carbon atoms (such as stearic acid or behenic acid) and corresponding amides, esters, or salts (such as magnesium stearate, zinc stearate, aluminum stearate, or magnesium behenate); quaternary ammonium compounds, such as tri[($C_1$–$C_4$ alkyl)benzyl]ammonium salts; plasticizers, such as epoxidized soya bean oil; waxes (such as polyethylene wax); resin acids (such as abietic acid, rosin soap, or hydrogenated or dimerized rosin); $C_{12}$–$C_{18}$-paraffin-disulfonic acids; sulfonated dicarboxylic acids and corresponding esters or amides thereof (such as sulfosuccinates, sulfosuccinamates, and derivatives thereof); alkyl phosphates and phosphonates; long chain fatty amines (such as laurylamine or stearylamine); polyamines (such as polyethylenimines); quaternary ammonium compounds (such as tri[($C_1$–$C_4$ alkyl)benzyl]-ammonium salts); alkylphenols; alcohols and diols (such as stearyl alcohol and dodecane-1,2-diol); alkoxylated fatty acids and amides, alkoxylated alcohols, alkoxylated alkylphenols, and glycol esters; polyurethanes; or combinations thereof. Such optional ingredients can be incorporated in amounts ranging up to about 20% by weight (preferably 0.05 to 20% by weight, more preferably 1 to 10% by weight), based on the amount of the perylene tetracarboxylic starting material of formula (III).

Step (a) is generally carried out at a temperature of about 50° C. to about 150° C., preferably for about two to about fifteen hours, more preferably about four to about seven hours.

The intermediate compositions formed in step (a) contain both unreacted perylene tetracarboxylic compounds of formula (III) and about 0.1 to about 25 mol %, relative to the total amount of the intermediate compositions, of perylene intermediates believed to be predominantly asymmetric dicarboxamidines having the formula (VI)

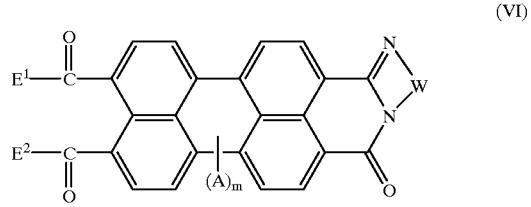

(VI)

wherein $E^1$, $E^2$, W, A, and m are defined as above. When using the preferred perylene dianhydride of formula (IIIa) as the perylene starting material, the perylene intermediate is believed to be predominantly asymmetric dicarboxamidine anhydride having the formula (VIa)

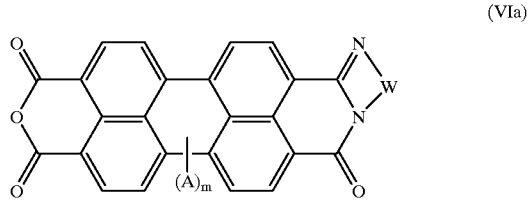

(VIa)

wherein W, A, and m are defined as above. The presence of small amounts of corresponding symmetric bis-dicarboxamidines, which is statistically more likely with increasing amounts of diamines of formula (IV), does not have an adverse effect on the properties of the ultimate product.

When using the perylene imide anhydride of formula (IIIb) as the perylene starting material, the perylene intermediate is believed to be an asymmetric perylene dicarboxamidine imide having the formula (II)

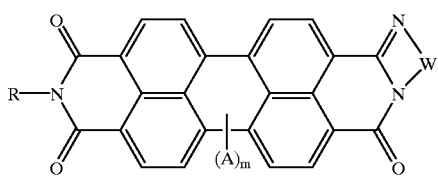

(II)

wherein R, W, A, and m are defined as above. Compounds of formula (II) are, of course, the asymmetric perylene dicarboxamidine imide component of the perylene pigment compositions of the invention and thus do not require further reaction. The unreacted imide anhydride must, however, still be converted to the perylene diimide component in step (b). Because dicarboxamidine imides of formula (II) are essentially insoluble after they are formed, the separate formation of the perylene diimide component during step (b) does not produce the same co-precipitate as that formed when using the preferred perylene dianhydrides of formula (IIIa).

Although generally much less preferred, particularly in view of the additional steps required, it is also possible to blend separately prepared batches of the perylene tetracarboxylic component of formula (III) and the asymmetric perylene dicarboxamidine anhydride of formula (VIa) as long as the resultant blend is subsequently allowed to react with monoamine of formula (V) in step (b). Compositions prepared,by blending already fully formed perylene diimides of formula (I) and asymmetric perylene dicarboxamidine imides of formula (II) would not exhibit the advantageous physical and color properties of compositions prepared according to the invention.

In step (b), the intermediate composition from step (a) is allowed to react with a monoamine of formula (V) in sufficient excess to convert all unreacted anhydride and/or ester groups of the perylene tetracarboxylic compounds of formula (III) and the perylene intermediates (believed to be asymmetric dicarboxamidines having formula (VI)) to imide groups.

Component (b)(ii) includes ammonia and primary amines having the formula R—$NH_2$ in which R is $C_1$–$C_6$ alkyl (preferably methyl), $C_7$–$C_{16}$ aralkyl, or $C_6$–$C_{10}$ aryl. Examples of suitable primary amines include alkylamines such as methyl amine, ethyl amine, propyl amine, butyl amine, pentyl amine, hexyl amine, and isomeric forms thereof; aralkylamines such as benzylamine and phenethylamine; and arylamines such as aniline, anisidine, phenetidine, toluidine, and various xylidine isomers. Use of methylamine in conjunction with a perylene tetracarboxylic compound having no A groups (e.g., unsubstituted perylene dianhydride), for example, gives rise to a perylene pigment composition containing as the principle component N,N'-dimethylperylenetetracarboxylic diimide (Pigment Red 179).

By appropriate selection of the amine of formula R—$NH_2$, it is possible to prepare pigment compositions in which the compound of formula (I) has two different R groups (i.e., an asymmetric perylene). For example, if the perylene tetracarboxylic compound of formula (III) is an imide in which $E^1$ and $E^2$ together are NR, step (b) can be carried out using an amine of formula R—$NH_2$ in which R is different from the already formed imide group.

It is necessary to use at least a slight excess of ammonia or primary amine relative to the anhydride and/or ester groups of the intermediate composition. The theoretical amount of monoamine required to complete the desired reaction can be calculated to account for the amount of unreacted anhydride and/or ester groups remaining in the mixture. However, it is generally preferred to use about 2.1 moles to about 5 mol of ammonia or primary amine per mol of the intermediate composition. Although generally not preferred, it is possible to use larger quantities of ammonia or primary amine, which, if liquid under the reaction conditions, can also serve as solvent or as co-solvent.

Step (b) is optionally carried out in a solvent. Suitable solvents (b)(iii) are liquids that are capable of dissolving or suspending the components of the reaction mixture without significantly decomposing or otherwise reacting during the reaction and can be the same as or different from (preferably the same as) the solvents used in step (a).

Conventional additives used with perylene pigments can also be added before or during reaction step (b). Examples of such additives include the additives mentioned above with respect to step (a). It is also possible to include compounds that react with monoamines of formula (V) to form pigment additives. Examples of suitable such reactive compounds include non-pigmentary cyclic anhydrides and imides such as those described in U.S. Pat. Nos. 6,015,458 and 6,039,769.

Step (b) is generally carried out at a temperature of about 50° C. to about 150° C., preferably for about two to about fifteen hours, more preferably about four to about seven hours.

During step (b), the perylene tetracarboxylic compounds and the perylene intermediates or transient intermediates that form during their conversion to compounds of formulas (I) and (II), respectively, are believed to become at least transiently soluble in the reaction medium. The asymmetric perylene dicarboxamidine imide component that forms during step (b) serves as a crystal growth inhibitor during the conversion of the intermediate mixtures to the perylene pigment compositions of the invention. Regardless of the exact nature of the process that occurs, it is the formation of a co-precipitated blend of compounds of formulas (I) and (II) during step (b) that is referred to herein as "reactive co-precipitation." The resultant reactive co-precipitated perylene pigment compositions have small-sized crystals having a relatively narrow particle size distribution and can be used to prepare paints having improved coloristic properties.

Although generally not necessary, final particle size of the pigment can thus be further controlled by varying the method of after treatment. For example, pigments can be made more transparent by reducing the particle size or more opaque by increasing the particle size. If desired, for example, the perylene pigment composition can be conditioned using methods known in the art, such as milling or, less preferably, solvent treatment or milling in combination with solvent treatment. Suitable milling methods include dry-milling methods such as jet milling, ball milling, and the like, with or without additives, or wet-milling methods such as salt kneading, sand milling, bead milling, and the like in water or organic solvents, with or without additives.

Use of various other optional ingredients during or after the optional conditioning step, although generally not necessary, can further improve properties of the perylene pigment compositions of the invention. Suitable optional ingredients include surfactants, dispersants, wetting agents, defoamers, grinding aids, latices, organic pigment derivatives, inorganic compounds (such as metal salts), or mixtures thereof, such as those mentioned above for use in step (a). Such optional ingredients can be incorporated in amounts ranging up to about 20% by weight (preferably 0.05 to 20% by weight, more preferably 1 to 10% by weight), based on the amount of the organic pigment composition.

Because of their advantageous properties, the perylene pigment compositions according to the present invention are suitable for many different pigment applications. For example, pigment compositions according to the invention can be used as the colorant (or as one of two or more colorants) for very lightfast pigmented systems. Examples include pigmented mixtures with other materials, pigment formulations, paints, printing ink, colored paper, or colored macromolecular materials. The term "mixtures with other materials" is understood to include, for example, mixtures with inorganic white pigments, such as titanium dioxide (rutile) or cement, or other inorganic pigments. Examples of pigment formulations include flushed pastes with organic liquids or pastes and dispersions with water, dispersants, and, if appropriate, preservatives. Examples of paints in which pigments of this invention can be used include, for example, physically or oxidatively drying lacquers, stoving enamels, reactive paints, two-component paints, solvent- or water-based paints, emulsion paints for weatherproof coatings, and distempers. Printing inks include those known for use in paper, textile, and tinplate printing. Suitable macromolecular substances include those of a natural origin, such as rubber; those obtained by chemical modification, such as acetyl cellulose, cellulose butyrate, or viscose; or those produced synthetically, such as polymers, polyaddition products, and polycondensates. Examples of synthetically produced macromolecular substances include plastic materials, such as polyvinyl chloride, polyvinyl acetate, and polyvinyl propionate; polyolefins, such as polyethylene and polypropylene; high molecular weight polyamides; polymers and copolymers of acrylates, methacrylates, acrylonitrile, acrylamide, butadiene, or styrene; polyurethanes; and polycarbonates. The materials pigmented with the perylene pigment compositions of the present invention can have any desired shape or form. The pigment compositions according to this invention are highly water-resistant, oil-resistant, acid-resistant, lime-resistant, alkali-resistant, solvent-resistant, fast to over-lacquering, fast to over-spraying, fast to sublimation, heat-resistant, and resistant to vulcanizing, yet give a very good tinctorial yield and are readily dispersible (for example, in plastic materials).

The following examples further illustrate details for the preparation and use of the compositions of this invention. The invention, which is set forth in the foregoing disclosure, is not to be limited either in spirit or scope by these examples. Those skilled in the art will readily understand that known variations of the conditions and processes of the following preparative procedures can be used to prepare these compositions. Unless otherwise noted, all temperatures are degrees Celsius and all percentages are percentages by weight.

EXAMPLES

Examples 1–5

Examples 1–5 describe the preparation of perylene pigment compositions that were analyzed for particle size characteristics.

Comparison Example 1 describes the preparation of N,N'-dimethyl-perylenetetracarboxylic diimide (Pigment Red 179) in the absence of a perylene dicarboxamidine imide according to the invention. Examples 2–4 describe the preparation of N,N'-dimethylperylenetetracarboxylic diimide in the presence of a perylene dicarboxamidine imide according to the invention.

Particle Size Test Methods

Particle sizes of the compositions prepared in the following examples were determined using QLS laser scattering, DCP disc centrifuge, and X-ray powder diffraction methods. For the laser scattering and disk centrifuge determinations, samples of each pigment composition were diluted in water, dispersed with an ultrasonic horn (600 W for two minutes), and further diluted. For the X-ray determinations, powder samples were used.

Laser scattering results were obtained using a Brookhaven Instruments Laser Scattering Particle Size Analyzer equipped with a BI-9000 Correlator detector using a photomultiplier tube voltage of 1.75 kV, a laser wavelength of 632.8 nm, a beam width of 1 mm (nonpolarized), a detection angle of 90°, and a cell length of 12 mm, and are reported as effective diameters ($D_{eff}$), which are similar to average or median values.

Disc centrifuge results were obtained using a Brookhaven Instruments BI-DCP 1000 Particle Sizer operating at 10,000 rpm and are reported as surface area average diameters ($D_s$), weight average diameters ($D_w$), 95% cumulative values in weight distribution ($D_{w,95}$), and polydispersity (the spread of the distribution defined as $D_w/D_n$, where $D_n$ is the number average diameter).

X-ray powder diffraction results were obtained using a Siemens D5000 X-Ray Diffractometer and are reported as full-width at half-maximum ("FWHM") for the singlet found at a diffraction angle 2θ of 8.2°.

Example 1 (Comparison)

A suspension of 120 g (0.31 mol) of perylene tetracarboxylic acid dianhydride ("PTCA") in 1600 g of water was heated with stirring to 90° C. and held at 90° C. for four hours. The suspension was then cooled to 23° C., after which 120 g (1.55 mol) of 40% aqueous monomethylamine solution was added dropwise over a period of 15 minutes. Once the addition was complete, the reaction mixture was stirred at 25° C. for another 45 minutes, heated to 80° C., and held at 80° C. for four hours. After being cooled to room temperature, the pigment was collected by vacuum filtration, washed free of amine, and dried to yield approximately 120 g of product.

Test results are shown in Table 1.

Example 2

A mixture of 450 g (1.15 mol) of PTCA, 6000 g of water, and 6 g (58.7 mmol) of 2,2-dimethyl-1,3-diaminopropane was stirred for one hour at 25° C., heated to 90° C., and held at 90° C. for 4 hours. The suspension was then cooled to 25° C., after which 450 g (5.81 mol) of 40% aqueous monomethylamine solution was added dropwise over a period of 15 minutes. Once the addition was complete, the reaction mixture was stirred at ambient temperature for another 45 minutes, heated to 80° C., and held at 80° C. for four hours. After being cooled to room temperature, the pigment was collected by vacuum filtration, washed free of amine, and dried to yield approximately 450 g of product containing about 5 mol % of an asymmetric perylene dicarboxamidine imide having the formula

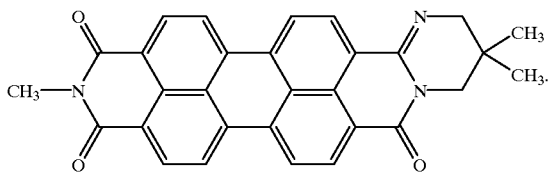

(VIa)

Test results are shown in Table 1.

Example 3

A mixture of 450 g (1.15 mol) of PTCA, 6000 g of water at 50° C., and 6 g (58.7 mmol) of 2,2-dimethyl-1,3-diaminopropane was heated with stirring to 90° C. and held at 90° C. for 4 hours. The suspension was then cooled to 25° C., after which 450 g (5.81 mol) of 40% aqueous monomethylamine solution was added dropwise over a period of 15 minutes. Once the addition was complete, the reaction mixture was stirred at ambient temperature for another 45 minutes, heated to 80° C., and held at 80° C. for four hours. After being cooled to room temperature, the pigment was collected by vacuum filtration, washed free of amine, and dried to yield approximately 450 g of product containing about 5 mol % of an asymmetric perylene dicarboxamidine imide having the formula

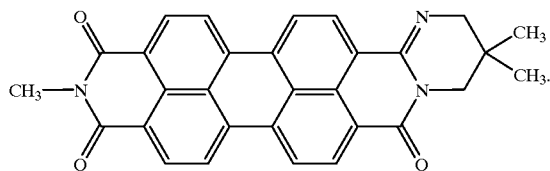

Test results are shown in Table 1.

Example 4

A mixture of 450 g (1.15 mol) of PTCA, 6000 g of water, and 4.68 g (51.9 mmol) of 1,3-diamino-2-hydroxypropane was stirred for one hour at 25° C., heated to 90° C., and held at 90° C. for 4 hours. The suspension was then cooled to 25° C., after which 450 g (5.81 mol) of 40% aqueous monomethylamine solution was added dropwise over a period of 15 minutes. Once the addition was complete, the reaction mixture was stirred at ambient temperature for another 45 minutes, heated to 80° C., and held at 80° C. for four hours. After being cooled to room temperature, the pigment was collected by vacuum filtration, washed free of amine, and dried to yield approximately 450 g of product containing about 4 mol % of an asymmetric perylene dicarboxamidine imide having the formula

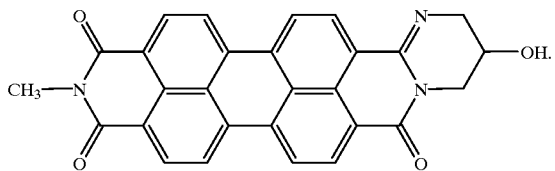

Test results are shown in Table 1.

Example 5

A mixture of 450 g (1.15 mol) of PTCA, 6000 g of water at 50° C., and 4.68 g (51.9 mmol) of 1,3-diamino-2-hydroxypropane was heated with stirring to 90° C. and held at 90° C. for 4 hours. The suspension was then cooled to 25° C., after which 450 g (5.81 mol) of 40% aqueous monomethylamine solution was added dropwise over the course of 15 minutes. Once the addition was complete, the reaction mixture was stirred at ambient temperature for another 45 minutes, heated to 80° C., and held at 80° C. for four hours. After being cooled to room temperature, the pigment was collected by vacuum filtration, washed free of amine, and dried to yield approximately 450 g of product containing about 4 mol % of an asymmetric perylene dicarboxamidine imide having the formula

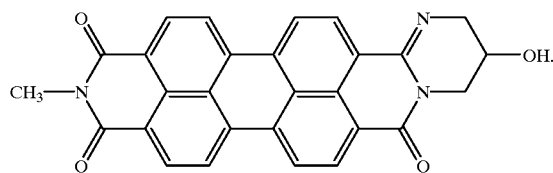

Test results are shown in Table 1.

TABLE 1

Particle size results for Examples 1–5

| Example | Laser scattering $D_{eff}$ (nm) | Disc centrifuge | | | | X-ray diffraction FWHM |
| --- | --- | --- | --- | --- | --- | --- |
| | | $D_s$ (nm) | $D_w$ (nm) | $D_{w,95}$ (nm) | Polydispersity | |
| 1 (comp) | 185 | 237 | 311 | 670 | 1.85 | 0.330 |
| 2 | 149 | 133 | 184 | 431 | 2.00 | 0.402 |
| 3 | 145 | 89 | 115 | 231 | 1.77 | 0.402 |
| 4 | 133 | 70 | 84 | 155 | 1.47 | 0.402 |
| 5 | 145 | 106 | 162 | 439 | 2.34 | 0.397 |

The test results presented in Table 1 show that pigment compositions prepared according to the invention have smaller particles that the comparison pigment prepared in the absence of a perylene dicarboxamidine imide.

Examples 6–8

Examples 6–8 describe the preparation of perylene pigment compositions that were further treated and tested for color properties in a aqueous paint system. In particular, Example 6 describes further conditioning of the pigment of comparison Example 1 and Examples 7 and 8 describe further conditioning of the pigments of Examples 2 and 4, respectively, for use in paint testing.

Paint Testing Method

Water-based paint tests were carried out on conditioned pigments described above using a waterborne basecoat/solvent-borne clearcoat paint system. Aqueous dispersions were prepared using a mixture of 12.4% AROLON® 559-G4-70 acrylic resin (Reichhold Chemicals, Inc.), 3.2% SOLSPERSE® 27000 hyperdispersant (Avecia, Inc.), 1.6% 2-amino-2-methyl-1-propanol (Angus Chemical), and 18% conditioned organic pigment which gave a pigment-to-binder ratio of 3:2 and a total solids content of 30%. The pigment-to-binder ratio was then reduced to 1:4 with additional AROLON® 559-G4-70 acrylic resin (total amount 26%) and 25% CYMEL® 325 melamine/formaldehyde resin (Cytec Industries), which gave a total solids content of 50%. Masstone and transparency measurements were made using films applied at 76 µm and 38 µm wet film thickness, respectively, and allowed to stand at room temperature for fifteen minutes and at 100° C. for five minutes. Clearcoats containing a mixture of 80% of AROPLAZ® 1453-X-50 alkyd resin (Reichhold Chemicals, Inc.) and 20% CYMEL® 325 melamine/formaldehyde resin at a total solids level of 57% were then applied over the basecoat at a 76 μm wet film thickness and allowed to stand at room temperature for fifteen minutes and at 121° C. for fifteen minutes.

Undertone tint paints were prepared from the reduced aqueous dispersions described above having a pigment-to-binder ratio of 1:4 by adding additional AROLON® 559-G4-70 acrylic resin, CYMEL® 325 melamine/formaldehyde resin, and 35% TINT-AYD® CW-5003 white dispersion (Elementis), which gave a pigment-to-binder ratio of 1:1.1, a total solids content of 55%, and a $TiO_2$-to-pigment ratio of 9:1. Color measurements were made using films applied at 38 μm wet film thickness and allowed to stand at room temperature for fifteen minutes and at 100° C. for five minutes. Clearcoats were then applied and baked as described above.

Metallic paints were prepared from the dispersion described above having a pigment-to-binder ratio of 3:2 using a water-dispersible aluminum pigment (available as HYDRO PASTE® 8726 from Silberline Manufacturing Co., Inc.), AROLON® 559-G4-70 acrylic resin, and CYMEL® 325 melamine/formaldehyde resin in quantities that provided a pigment-to-binder ratio of 1:2, an aluminum-to-pigment ratio of 1:4, and a total solids content of 43%. Color measurements were made using films applied at 38 μm wet film thickness and baked as described above. Clearcoats were then applied and baked as described above.

The coloristic values for paints containing the conditioned organic pigments were obtained on a CS-5 Chroma Sensor spectrometer from Datacolor International using a D65 illuminant at an angle of 10 degrees. All values for ΔL, ΔH, ΔC, and transparency were measured relative to the comparison pigment prepared according to Example 6. Positive values for ΔL, ΔH, ΔC, and transparency correspond to lighter, yellower, more chromatic, and more transparent samples, respectively. Subjective qualitative evaluations of flop were determined by a skilled observer.

The conditioned pigment was used as the control pigment for color testing of the pigments of Examples 7 and 8, for which the results are given in Table 2.

Example 7

To an approximately 895-g sample of the perylene dicarboxamidine imide of Example 2 in presscake form (approximately 25% solids, 215 g of pigment) was added 32.25 g of SOLSPERSE® 27000. The slurry was stirred for one hour to generate a homogeneous slurry that was then added to a horizontal media mill charged with 0.3 to 0.4 mm zirconium silicate beads and milled for five hours. Due to addition of water during the charging of the slurry to the mill, the solids content at the conclusion of the milling was 22.95%. After milling was complete, the mill was discharged and rinsed with water and the combined slurry and wash water was spray dried to yield 236.29 g of conditioned pigment.

Color properties relative to the comparison pigment of Example 6 are given in Table 2.

Example 8

To an approximately 884-g sample of the perylene dicarboxamidine imide of Example 4 in presscake form (approximately 25% solids, 221 g of pigment) was added 33.15 g of SOLSPERSE® 27000. The slurry was stirred for one hour to generate a homogeneous slurry that was then added to a horizontal media mill charged with 0.3 to 0.4 mm zirconium silicate beads and milled for five hours. Due to addition of water during the charging of the slurry to the mill, the solids content at the conclusion of the milling was 22.58%. After milling was complete, the mill was discharged and rinsed with water and the combined slurry and wash water was spray dried to yield 213.36 g of conditioned pigment.

Color properties relative to the comparison pigment of Example 6 are given in Table 2.

TABLE 2

Color property test results for Examples 7 and 8 relative to comparison Example 6

| Example | Masstone | | | Undertone | | | | Aluminum metallic | | | | |
| --- | --- | --- | --- | --- | --- | --- | --- | --- | --- | --- | --- | --- |
| | ΔL | ΔC | Trans. | ΔL | ΔH | ΔC | % str. | ΔL | ΔH | ΔC | % str. | Flop |
| 7 | −0.74 | −3.14 | 0.45 | −1.07 | 0.30 | 0.47 | 98.32 | 0.49 | 0.27 | 1.67 | 104.79 | deep |
| 8 | −1.69 | −6.23 | 1.58 | 0.30 | 1.82 | 1.96 | 113.70 | 2.13 | 1.97 | 5.25 | 112.05 | deep |

Examples 6 (Comparison)

To a 295.53 g sample of the comparison pigment of Example 1 in presscake form (20 to 40% solids, 60.28 g of pigment) was added 9.04 g of a nonionic aromatic ethoxylate dispersant available as SOLSPERSE® 27000 from Avecia. The slurry was stirred for one hour to generate a homogeneous slurry that was then added to a horizontal media mill charged with 0.3 to 0.4 mm zirconium silicate beads and milled for five hours. Due to water evaporation during the milling, the solids content at the conclusion of the milling was 20.89%. After milling was complete, the mill was discharged and rinsed with water and the combined slurry and wash water was spray dried to yield 62.27 g of conditioned pigment.

The test results presented in Table 2 show that water-based paints prepared using pigment compositions prepared according to the invention exhibit a deeper and more transparent masstone, a yellower and cleaner undertone (tint), and stronger, cleaner, and yellower metallics when compared to paints prepared using the comparison pigment of Example 1.

What is claimed is:

1. A perylene pigment composition comprising a reactive co-precipitated blend comprising (1) about 75 to about 99.9 mol %, relative to the pigment composition, of a compound having the formula

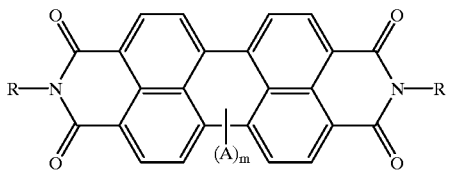

wherein
each R is independently hydrogen, $C_1$–$C_6$ alkyl, $C_5$–$C_8$ cycloalkyl, $C_7$–$C_{16}$ aralkyl, or $C_6$–$C_{10}$ aryl,
A is $C_1$–$C_6$ alkyl, $C_1$–$C_6$ alkoxy, a sulfonyl group, amino, ammonium, hydroxy, nitro, or halogen, and m is zero or a number from 1 to 8; and (2) about 0.1 to about 25 mol %, relative to the pigment composition, of a perylene dicarboxamidine imide having the formula

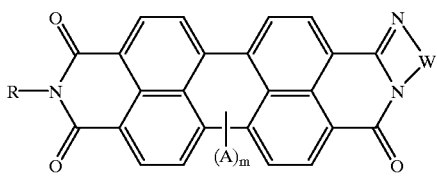

wherein
W is $C_2$–$C_3$ alkylene that is optionally substituted or modified,
R is hydrogen, $C_1$–$C_6$ alkyl, $C_5$–$C_8$ cycloalkyl, $C_7$–$C_{16}$ aralkyl, or $C_6$–$C_{10}$ aryl,
A is $C_1$–$C_6$ alkyl, $C_1$–$C_6$ alkoxy, a sulfonyl group, amino, ammonium, hydroxy, nitro, or halogen, and m is zero or a number from 1 to 8.

2. A perylene pigment composition according to claim 1 wherein m is zero.

3. A perylene pigment composition according to claim 1 wherein W is 1,3-diaminopropane or 1,3-diaminopropane substituted in the 2-position with one or two $C_1$–$C_6$ alkyl groups or a hydroxy group.

4. A perylene pigment composition according to claim 1 wherein R is $C_1$–$C_6$ alkyl.

5. A process for preparing a perylene pigment composition according to claim 1 comprising (a) reacting (i) a perylene tetracarboxylic compound having the formula (III)

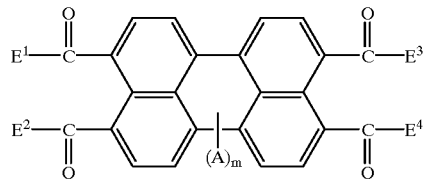

wherein
$E^1$ and $E^2$ are independently $OR^1$ or together are O or NR,
$E^3$ and $E^4$ are independently $OR^1$ or together are O, each $R^1$ is independently $C_1$–$C_6$ alkyl, $C_7$–$C_{16}$ aralkyl, or $C_6$–$C_{10}$ aryl,
R is hydrogen, $C_1$–$C_6$ alkyl, $C_5$–$C_8$ cycloalkyl, $C_7$–$C_{16}$ aralkyl, or $C_6$–$C_{10}$ aryl,
A is $C_1$–$C_6$ alkyl, $C_1$–$C_6$ alkoxy, a sulfonyl group, amino, ammonium, hydroxy, nitro, or halogen, and m is zero or an integer of from 1 to 8, (ii) about 0.1 to about 25 mol %, based on the total amount of component (a)(i), of a diamine having the formula (IV)

$$H_2N—W—NH_2 \qquad (IV)$$

wherein W is $C_2$–$C_3$ alkylene that is optionally substituted or modified, and (iii) optionally, a solvent, thereby forming an intermediate composition;

(b) reacting (i) the intermediate composition from step (a), (ii) a molar excess, relative to the intermediate composition, of an amine having the formula (V)

$$R—NH_2 \qquad (V)$$

wherein R is hydrogen, $C_1$–$C_6$ alkyl, $C_5$–$C_8$ cycloalkyl, $C_7$–$C_{16}$ aralkyl, or $C_6$–$C_{10}$ aryl, and (iii) optionally, a solvent, thereby forming the perylene pigment composition as a reactive co-precipitated blend comprising a compound of formula (I) and an asymmetric perylene dicarboxamidine imide of formula (II); and (c) isolating the perylene pigment composition.

6. A process according to claim 5 wherein $E^1$ and $E^2$ together and $E^3$ and $E^4$ together are oxygen atoms.

7. A process according to claim 5 wherein W is 1,3-diamino-propane or 1,3-diaminopropane substituted in the 2-position with one or two $C_1$–$C_6$ alkyl groups or a hydroxy group.

8. A process according to claim 5 wherein R is $C_1$–$C_6$ alkyl.

9. A process according to claim 5 wherein m is zero.

10. A process according to claim 5 wherein steps (a) and (b) are carried out using water as solvent.

* * * * *